United States Patent
Sandhu et al.

(10) Patent No.: US 6,628,451 B2
(45) Date of Patent: Sep. 30, 2003

(54) ACOUSTO-OPTIC REFLECTION-ACTIVE IMAGING

(76) Inventors: Jaswinder S Sandhu, 454 Carman Ave., Buffalo Grove, IL (US) 60089; Honghui Wang, 341 S. Jewel Ct., Palatine, IL (US) 60067

( * ) Notice: Subject to any disclaimer, the term of this patent is extended or adjusted under 35 U.S.C. 154(b) by 0 days.

(21) Appl. No.: 10/076,187

(22) Filed: Feb. 14, 2002

(65) Prior Publication Data

US 2003/0151794 A1 Aug. 14, 2003

(51) Int. Cl.$^7$ .................................................. G02F 1/11
(52) U.S. Cl. .............................. 359/285; 359/305; 385/7
(58) Field of Search .................................. 359/285, 305; 348/754, 769; 385/7; 372/13; 356/364, 365, 366; 73/603, 606, 618

(56) References Cited

U.S. PATENT DOCUMENTS

| | | | | | |
|---|---|---|---|---|---|
| 4,093,976 A | * | 6/1978 | Das | .............................. | 348/196 |
| 4,727,420 A | * | 2/1988 | Kohda et al. | ................ | 348/163 |
| 5,796,003 A | | 8/1998 | Sandhu | ......................... | 73/603 |
| 6,049,411 A | | 4/2000 | Sandhu | ......................... | 359/285 |
| 2003/0016434 A1 | * | 1/2003 | Torchigin | .................... | 359/286 |

* cited by examiner

*Primary Examiner*—Ricky Mack
*Assistant Examiner*—Brandi Thomas
(74) *Attorney, Agent, or Firm*—Don Moyer

(57) ABSTRACT

A product and method uses acousto-optic reflection-active media having an optical reflectivity which changes with changes in acoustic energy intensity interacting with the media to form images of defects in samples when the defects reflect acoustic energy differently from known acoustically reflecting parts of the samples.

8 Claims, 1 Drawing Sheet

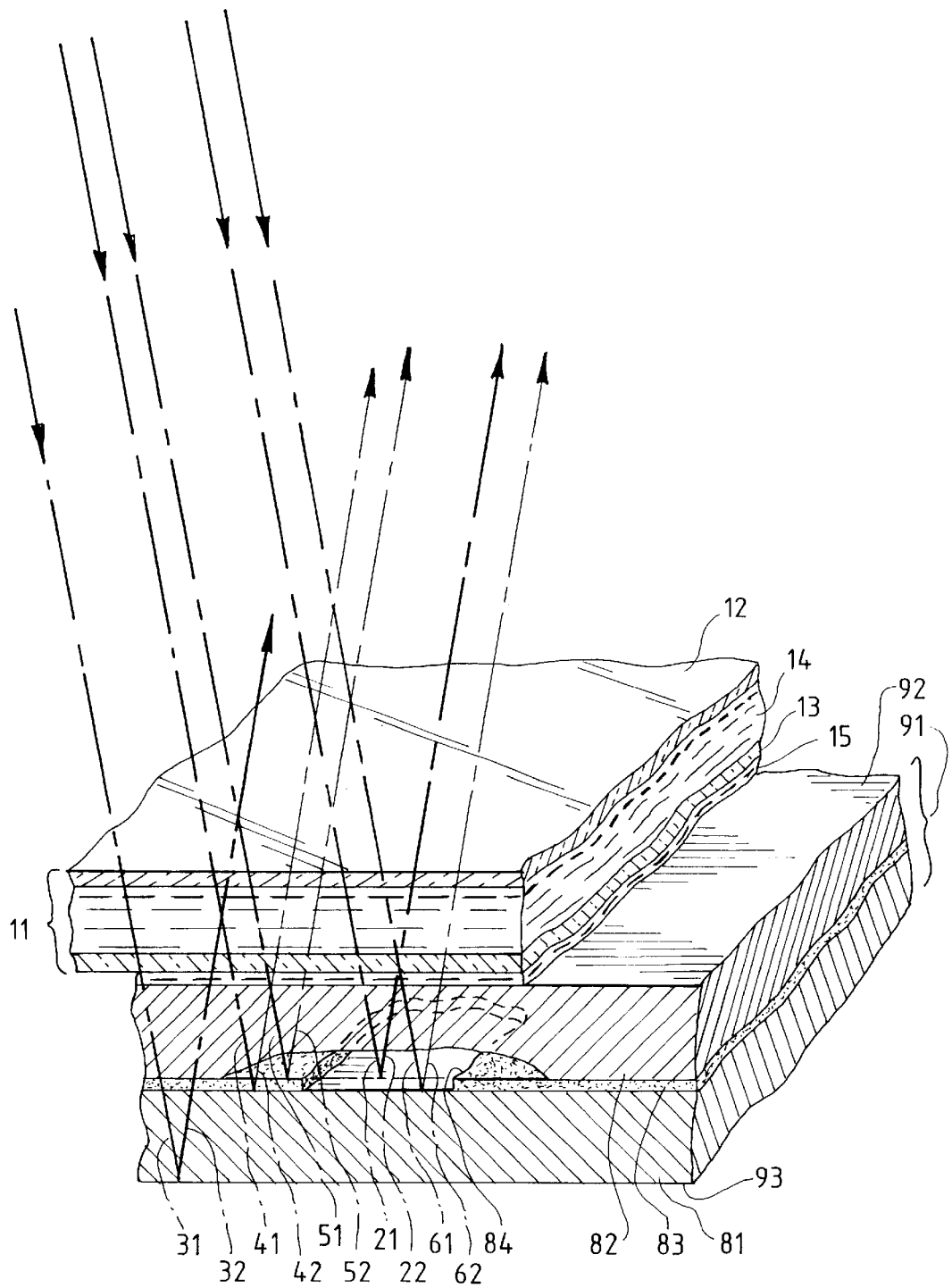

ACOUSTO-OPTIC REFLECTION-ACTIVE IMAGING

Acousto-optic reflection-active media have an optical reflectivity which changes with changes in acoustic energy intensity interacting with the media and form images of defects in samples when the defects reflect acoustic energy differently from known acoustically reflecting parts of the samples.

Acousto-optic reflection-active media were not expected. This activity is surprising because incident acoustic energy enters the media along with reflected acoustic energy. It was expected that the effect of incident acoustic energy interacting with the media would overwhelm the effect of reflected acoustic energy interacting with the medium. Acousto-optic reflection-active media have an optical reflectivity which changes with changes in reflected acoustic energy intensity interacting with the media even though incident acoustic energy is also interacting with the media—which thus defines acousto-optic reflection-active media.

The product provides progress over prior art for example shown by Sandhu in U.S. Pat. Nos. 6,049,411 and 5,796,003 and by the art disclosed there.

The FIG. depicts—in cross section with cutaways—acoustic energy incident on a sample having known acoustically reflecting parts and having a defect and depicts reflected acoustic energy reflected into an acousto-optic reflection-active medium.

In acousto-optic reflection-active imaging acoustic, energy is reflected by a sample 91 which has a sample near surface 92, a sample far surface 93, and a sample defect 84. The reflected acoustic energy enters an acousto-optic reflection-active medium 14 which is contained between an imager near surface 13 and an imager far surface 12. The imager near surface is proximal the sample near surface.

Surprisingly, acousto-optic reflection-active media have an optical reflectivity which changes with changes in acoustic energy intensity reflected into the medium. The medium can have positive acousto-optic reflection-activity where an optical reflectivity increases as acoustic energy intensity interacting with the medium increases.

Surprisingly, media used in transmission-mode acoustic imaging are also acousto-optic reflection-active media. For example the birefringent liquid crystal 4-cyano-4'-n-pentyl biphenyl has a positive acousto-optic reflection-activity. Any media which are acousto-optic reflection-active media having an optical reflectivity which changes with changes in intensity of acoustic energy interacting with the media can be used.

The figure shows an imager 11 where the medium is contained between two plates with the imager near surface 13 being acoustically coupled with the sample near surface via a coupling medium 15. Other configurations are possible. An imager near surface can be directly in contact with the sample near surface.

Acousto-optic reflection-active media can be self contained, with the imager far surface and the imager near surface being surfaces of the media itself. These media can be acoustically coupled with the sample near surface via a coupling medium and can be directly in contact with the sample near surface.

Incident acoustic energy radiates away from the sample near surface toward the sample far surface as depicted by the ray lines 21, 31, 41, 51, 61. Incident acoustic energy can originate distal the imager near surface and proximal the imager far surface. Incident acoustic energy can originate from anywhere between the imager far surface and the defect.

The acoustic energy source can be any which produces acoustic energy which can activate the acousto-optic reflection-active medium. The acoustic energy source can have a source area equal to the imager area. The acoustic energy source can have a source area smaller—and larger—than the imager area. The acoustic energy source can be scanned over the imager area. For example, incident acoustic energy can be provided by means such as those described in U.S. Pat. Nos. 5,796,003 and 6,049,411 and described in the art disclosed there.

The sample shown has two portions 81 and 82 bonded together by an adhesive 83. The defect 84 here is an absence of bonding material. Defects in samples with only one portion and samples with more than two bonded portions can be imaged by the product and method described here. All that is required is that there be a difference between acoustic energy reflected by a defect and reflected by known acoustically reflective parts of a sample.

Defects can be any undesired substance, lack of substance, structure, or lack of structure in a sample. Defects which do not reflect acoustic energy differently from known acoustically reflecting parts and defects which are masked by other defects will not be detected.

Expected acoustic energy is an expected portion of the incident acoustic energy which has been reflected at known sample parts which are acoustically reflective—such as the bond interfaces and the sample far surface. The expected acoustic energy radiates through the imager near surface as depicted by the ray lines 32, 42, 52. Of these, the acoustic energy reflected at the sample to air interface at the sample far surface 93 is by far the highest intensity.

Defect acoustic energy is a defect portion of the incident acoustic energy which has been reflected at the defect and radiates through the imager near surface as depicted by the ray lines 22, 62. Of these the acoustic energy reflected at the sample to defect interface is by far the largest because very little acoustic energy gets to the defect to sample interface.

While there will be many reflections of reflections, the sample far reflection 32 will dominate the expected acoustic energy. Defects which reflect more acoustic energy than the far reflection into the active medium, and defects which reflect less acoustic energy than the far reflection into the active medium can be detected.

An image is formed by the acousto-optic reflection-active medium when there are acoustic energy intensity differences between the expected acoustic energy and the defect acoustic energy. When the imager medium has a positive acousto-optic property and the defect acoustic energy intensity is greater than the expected acoustic energy intensity, then the image is a portion of the imager which is darker than the surrounding portion. With this medium when the defect acoustic energy intensity is less than the expected acoustic energy intensity, then the image is a portion of the imager which is lighter than the surrounding portion.

The medium is viewable from the imager far surface 12. Viewing can be by direct vision, can be via various imaging means, and can be via various data acquisition means.

When media used in transmission-mode acoustic imaging—such as the birefringent liquid crystal 4cyano-4'-n-pentyl biphenyl—are used as the acousto-optic reflection-active medium, then the imager is viewed as described by Sandhu in U.S. Pat. No. 6,049,411 which is incorporated herein by reference.

Experiments indicate that other materials are acousto-optic reflection-active and that materials can be tailored to meet specific imaging needs. Experiments indicate that large area acousto-optic reflection-active imagers can be made and that these can be made flexible.

The invention comprises an acousto-optic reflection-active imaging method as well as an acousto-optic reflection-active imaging product. Both the product and the method utilize the elements, connections, and causes described above.

The method comprises radiating incident acoustic energy away from a sample near surface toward a sample far surface so that expected acoustic energy and defect acoustic energy radiate toward the sample near surface, and comprises interacting the expected acoustic energy and the defect acoustic energy with an acousto-optic reflection-active medium having an optical reflectivity which changes with changes in acoustic energy intensity interacting with the medium.

The expected acoustic energy is an expected portion of the incident acoustic energy which has been reflected at known sample parts which are acoustically reflective. The defect acoustic energy is a defect portion of the incident acoustic energy which has been reflected at the defect.

The medium is contained between an imager near surface and an imager far surface. The imager near surface is proximal the sample near surface. An image is formed by the acousto-optic reflection-active medium when there are acoustic energy intensity differences between the expected acoustic energy and the defect acoustic energy.

What is claimed is:

1. An acoustic-optic imaging product which images acoustic energy reflected by a sample, the sample having a sample near surface, a sample far surface, and a sample defect, the product comprising:
   an acousto-optic reflection-active medium having an optical reflectivity which changes with changes in acoustic energy intensity interacting with the medium
   the medium being contained between an imager near surface and an imager far surface,
   the imager near surface being proximal the sample near surface,
   the imager being viewable from the far surface;
   incident acoustic energy,
   the incident acoustic energy radiating away from the sample near surface toward the sample far surface;
   expected acoustic energy,
   the expected acoustic energy being an expected portion of the incident acoustic energy which has been reflected at known sample parts which are acoustically reflective
   the expected acoustic energy radiating through the imager near surface;
   defect acoustic energy,
   the defect acoustic energy being a defect portion of the incident acoustic energy which has been reflected at the defect,
   the defect acoustic energy radiating through the imager near surface; and
   an image being formed by the acousto-optic reflection-active medium when there are acoustic energy intensity differences between the expected acoustic energy and the defect acoustic energy.

2. The product of claim 1 wherein the incident acoustic energy originates distal the imager near surface and proximal the imager far surface.

3. The product of claim 1 wherein the incident acoustic energy originates between the imager far surface and the defect.

4. An acoustic-optic imaging product which images acoustic energy reflected by a sample, the sample having a sample near surface, a sample far surface, and a sample defect, the product comprising:
   an acousto-optic reflection-active medium having an optical reflectivity which changes with changes in acoustic energy intensity interacting with the medium
   the medium being contained between an imager near surface and an imager far surface,
   the imager near surface being proximal the sample near surface,
   the imager being viewable from the far surface;
   incident acoustic energy,
   the incident acoustic energy originating distal the imager near surface and proximal the imager far surface,
   the incident acoustic energy radiating away from the sample near surface toward the sample far surface;
   expected acoustic energy,
   the expected acoustic energy being an expected portion of the incident acoustic energy which has been reflected at known sample parts which are acoustically reflective
   the expected acoustic energy radiating through the imager near surface;
   defect acoustic energy,
   the defect acoustic energy being a defect portion of the incident acoustic energy which has been reflected at the defect,
   the defect acoustic energy radiating through the imager near surface; and
   an image being formed by the acousto-optic reflection-active medium when there are acoustic energy intensity differences between the expected acoustic energy and the defect acoustic energy.

5. An acoustic-optic imaging method which images acoustic energy reflected by a sample, the sample having a sample near surface, a sample far surface, and a sample defect, the method comprising:
   radiating incident acoustic energy away from the sample near surface toward the sample far surface so that expected acoustic energy and defect acoustic energy radiate toward the sample near surface, where:
      the expected acoustic energy is an expected portion of the incident acoustic energy which has been reflected at known sample parts which are acoustically reflective,
      the defect acoustic energy is a defect portion of the incident acoustic energy which has been reflected at the defect; and
   interacting the expected acoustic energy and the defect acoustic energy with an acousto-optic reflection-active medium having an optical reflectivity which changes with changes in acoustic energy intensity interacting with the medium where:
      the medium is contained between an imager near surface and an imager far surface,
      the imager near surface is proximal the sample near surface.

6. The method of claim 5 further comprising originating the incident acoustic energy distal the imager near surface and proximal the imager far surface.

7. The method of claim 5 further comprising originating the incident acoustic energy from between the imager far surface and the defect.

8. An acoustic-optic imaging method which images acoustic energy reflected by a sample, the sample having a sample near surface, a sample far surface, and a sample defect, the method comprising:

radiating incident acoustic energy away from the sample near surface toward the sample far surface so that expected acoustic energy and defect acoustic energy radiate toward the sample near surface, where:
the incident acoustic energy originates distal the imager near surface and proximal the imager far surface
the expected acoustic energy is an expected portion of the incident acoustic energy which is reflected at known sample parts which are acoustically reflective,
the defect acoustic energy is a defect portion of the incident acoustic energy reflected at the defect; and
interacting the expected acoustic energy and the defect acoustic energy with an acousto-optic reflection-active medium having an optical reflectivity which changes with changes in acoustic energy intensity interacting with the medium where:
the medium is contained between an imager near surface and an imager far surface, and
the imager near surface is proximal the sample near surface.

* * * * *